United States Patent
Carlson et al.

(10) Patent No.: US 7,881,502 B2
(45) Date of Patent: Feb. 1, 2011

(54) METHOD AND SYSTEM FOR THREE-DIMENSIONALLY IMAGING AN APICAL DOME OF A PLANT EMBRYO

(75) Inventors: William Carlson, Olympia, WA (US); Edwin Hirahara, Federal Way, WA (US); Paul Roger Spencer, Pullman, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 955 days.

(21) Appl. No.: 10/852,765

(22) Filed: May 21, 2004

(65) Prior Publication Data

US 2004/0268445 A1    Dec. 30, 2004

Related U.S. Application Data

(60) Provisional application No. 60/560,718, filed on Jun. 30, 2003.

(51) Int. Cl.
*G06K 9/00* (2006.01)
(52) U.S. Cl. .................. 382/110; 382/224; 356/609
(58) Field of Classification Search .......... 382/110, 382/224; 356/609
See application file for complete search history.

(56) References Cited

U.S. PATENT DOCUMENTS

| | | | |
|---|---|---|---|
| 5,659,623 A * | 8/1997 | Conrad | 382/110 |
| 5,703,784 A | 12/1997 | Pearson | |
| 5,784,158 A * | 7/1998 | Stanco et al. | 356/326 |
| 6,094,300 A * | 7/2000 | Kashima et al. | 359/385 |
| 6,145,247 A | 11/2000 | McKinnis | |
| 6,160,908 A * | 12/2000 | Hakozaki | 382/154 |

(Continued)

FOREIGN PATENT DOCUMENTS

WO    WO 99/22220 A1    5/1999

(Continued)

OTHER PUBLICATIONS

Cohen-Sabban et al., "Quasi Confocal Extended Field Surface Sensing", Dec. 2001, SPIE, vol. 4449, 178-183.*

(Continued)

*Primary Examiner*—Vikkram Bali
*Assistant Examiner*—Katrina Fujita
(74) *Attorney, Agent, or Firm*—Christenson O'Connor Johnson Kindness PLLC

(57) ABSTRACT

Methods and systems for three-dimensionally imaging an apical dome located at the cotyledon end of a plant embryo are provided. Three-dimensional information of an apical dome can be obtained by scanning the apical dome at varying focal planes along an axis of the embryo, or by using multiple cameras arranged in a confocal manner to image the apical dome. It can also be obtained by irradiating the apical dome with polychromatic light, wherein light beams of multiple wavelengths are focused at multiple focal planes along the axis of the embryo so that the dome's height information can be obtained based on the wavelength of the light precisely focused and reflected at each surface point of the dome. The three-dimensional information is used to ascertain various morphological features (e.g., size, shape, texture, etc.) of the apical dome, which are in turn used to assess the embryo's germinant vigor.

20 Claims, 2 Drawing Sheets

U.S. PATENT DOCUMENTS

| | | | |
|---|---|---|---|
| 6,399,935 B1 * | 6/2002 | Jovin et al. | 250/216 |
| 6,687,052 B1 * | 2/2004 | Wilson et al. | 359/385 |
| 7,289,646 B2 * | 10/2007 | Hirahara et al. | 382/110 |
| 2003/0086067 A1 | 5/2003 | Gerstner et al. | |
| 2005/0069176 A1 * | 3/2005 | Toland | 382/110 |

FOREIGN PATENT DOCUMENTS

| | | |
|---|---|---|
| WO | WO 99/63057 A1 | 12/1999 |
| WO | 01/13702 A1 | 3/2001 |
| WO | WO 02/12945 A2 | 2/2002 |

OTHER PUBLICATIONS

Stasolla et al. "Maturation of Somatic Embryos in Conifers: Morphogenesis, Physiology, Biochemistry, and Molecular Biology", 2002, In Vitro Cellular & Developmental Biology—Plant, 93-105.*

Prevrhal et al. "Three-dimensional Assessment of Bone Turnover Using Computer Microtomography and Laser-Scanning Confocal Microscopy", 2000, Medical Imaging 2000: Image Processing, 1396-1403.*

Grob Ja, et al., "Dimensional Model of Zygotic Douglas-Fir Embryo Development," Intl J Plant Sci 160(4):653-662,1999.

Romberger Ja et al., "The Shoot Apical Ontogency of the Picea Abies Seedling: III. Some Age-Related Aspects of Morphogenesis," Amer J Bot 64(6):622-630, 1977.

Elster R, "Analysis of four *embryo-specific* mutants in *Zeas mays* revelas that incomplete radial organization of the proembryo interferes with subsequent development," *Dev Genes Evol* 2000 210:300-310.

Ibaraki Y et al., "Automation of somatic embryo production," *Plant Cell Tissue & Organ Cult* 65: 179-199, 2001.

Prevrhal A. et al: "Three-dimensional assessment of bone turnover using computed microtomography and laser-scanning confocal microscopy" Processing of the SPIE—The International Society for Optical Entineering SPIE-Int. Soc. Opt. Ing USA, vol. 3979, 2000, pp. 1396-1403, ISSN: 0277-786X.

* cited by examiner

METHOD AND SYSTEM FOR THREE-DIMENSIONALLY IMAGING AN APICAL DOME OF A PLANT EMBRYO

CROSS REFERENCE TO RELATED APPLICATION

The present application claims the benefit of U.S. Provisional Application No. 60/560,718, filed Jun. 30, 2003.

FIELD OF THE INVENTION

The invention is directed to imaging plant embryos for determination of suitability for further treatments, and more particularly, to three-dimensionally imaging an apical dome located at the cotyledon end of a plant embryo so as to permit selection of an embryo suitable for incorporation into a manufactured seed based on the ascertained morphological features of the dome.

BACKGROUND OF THE INVENTION

Reproduction of selected plant varieties by tissue culture has been a commercial success for many years. The technique has enabled mass production of genetically identical selected ornamental plants, agricultural plants and forest species. The woody plants in this last group have perhaps posed the greatest challenges. Some success with conifers was achieved in the 1970s using organogenesis techniques wherein a bud, or other organ, was placed on a culture medium where it was ultimately replicated many times. The newly generated buds were placed on a different medium that induced root development. From there, the buds having roots were planted in soil.

While conifer organogenesis was a breakthrough, costs were high due to the large amount of handling needed. There was also some concern about possible genetic modification. It was a decade later before somatic embryogenesis achieved a sufficient success rate so as to become the predominant approach to conifer tissue culture. With somatic embryogenesis, an explant, usually a seed or seed embryo, is placed on an initiation medium where it multiplies into a multitude of genetically identical immature embryos. These can be held in culture for long periods and multiplied to bulk up a particularly desirable clone. Ultimately, the immature embryos are placed on a development or maturation medium where they grow into somatic analogs of mature seed embryos. As used in the present description, a "somatic" embryo is a plant embryo developed by the laboratory culturing of totipotent plant cells or by induced cleavage polyembryogeny, as opposed to a zygotic embryo which is a plant embryo removed from a seed of the corresponding plant. These embryos are then individually selected and placed on a germination medium for further development. Alternatively, the embryos may be used in artificial seeds, known as manufactured seeds.

There is now a large body of general technical literature and a growing body of patent literature on embryogenesis of plants. Examples of procedures for conifer tissue culture are found in U.S. Pat. Nos. 5,036,007 and 5,236,841 to Gupta et al.; U.S. Pat. No. 5,183,757 to Roberts; U.S. Pat. No. 5,464,769 to Attree et al.; and U.S. Pat. No. 5,563,061 to Gupta. Further, some examples of manufactured seeds can be found in U.S. Pat. No. 5,701,699 to Carlson et al., the disclosure of which is hereby expressly incorporated by reference. Briefly, a typical manufactured seed is formed of a seed coat (or a capsule) fabricated from a variety of materials such as cellulosic materials, filled with a synthetic gametophyte (a germination medium), in which an embryo surrounded by a tube-like restraint is received. After the manufactured seed is planted in the soil, the embryo inside the seed coat develops roots and eventually sheds the restraint along with the seed coat during germination.

One of the more labor intensive and subjective steps in the embryogenesis procedure is the selection of individual embryos suitable for germination (e.g., incorporation into manufactured seeds). The embryos harvested from the maturation medium may be present in a number of stages of maturity and development. Those that are most likely to successfully germinate and grow into normal plants are preferentially selected using a number of visually evaluated screening criteria. Morphological features such as axial symmetry, cotyledon development, surface texture, color, and others are examined and applied as a pass/fail test before the embryos are passed on for germination. This is a skilled yet tedious manual labor that is time consuming and expensive. Further, it poses a major production bottleneck when the ultimate desired output will be in the millions of plants.

It has been proposed to use some form of instrumental image analysis for embryo selection to supplement or replace the visual evaluation described above. For example, PCT application Ser. No. PCT/US00/40720 (WO 01/13702 A2) discloses an embryo delivery system for manufactured seeds including an imaging camera, which acquires and digitally stores images of embryos. The images are then sent to a computer, which classifies the embryos according to their desirability (i.e., likelihood to germinate and grow into normal plants) based on predetermined parameters (axial symmetry, cotyledon development, surface texture, color, etc.) using a classification method disclosed in PCT application Ser. No. PCT/US99/12128 (WO 99/63057). Typically, three orthogonal views of an embryo (typically of up to about 5 mm in length) are imaged and analyzed, namely, a top view, a side view, and an end view. The disclosure of these two PCT applications is hereby expressly incorporated by reference.

The present invention is directed to a method and system for supplementing the current instrumental imaging analysis, to further the efficiency and effectiveness of the overall approach for classifying embryos according to their desirability, in particular for incorporation into manufactured seeds.

SUMMARY OF THE INVENTION

The present invention offers a method and system for three-dimensionally imaging an apical dome of a plant embryo. The invention is based on the determination that various morphological features of an apical dome (size, volume, shape, etc.) are reliable indicators of the embryo's putative germinant vigor (i.e., potential for rapid epicotyl development after germination). The method includes generally three steps. First, three-dimensional information of an apical dome of a plant embryo is obtained. Second, morphological features of the apical dome are ascertained based on the three-dimensional information. Third, the embryos are classified according to their putative germinant vigor based on the ascertained morphological features.

Various systems may be used to obtain three-dimensional information of an apical dome. In one embodiment, a system includes an image detector arranged relative to an apical dome of a plant embryo. The image detector is configured to take multiple images of the apical dome at varying focal planes, respectively, along an axis of the embryo. The multiple two-dimensional images thusly obtained are then combined to produce three-dimensional information of the apical dome.

In another embodiment, a system for obtaining three-dimensional information of an apical dome includes multiple image detectors arranged in a confocal manner, wherein object planes of the multiple image detectors are at an angle with respect to each other. The images taken by these multiple image detectors can be processed to obtain three-dimensional information of the apical dome.

In yet another embodiment, a system for obtaining three-dimensional information of an apical dome includes a polychromatic light source, a dichroic mirror, a lens with chromatic aberration, and a spectrometer arranged relative to each other so that polychromatic light from the light source propagates via the dichroic mirror and the lens toward an apical dome and so that light reflected from the apical dome propagates back via the lens and the dichroic mirror toward the spectrometer. In operation, the light source is used to irradiate the apical dome with the polychromatic light. Because light beams of multiple wavelengths are focused at multiple focal planes along an axis of the embryo for a lens with chromatic aberration, at any given point along an axial field of view, there is only one wavelength perfectly focused and reflected back to the spectrometer. Therefore, by processing the reflected light, accurate height information of the apical dome can be obtained.

Any system of the present invention for three-dimensionally imaging an apical dome of each embryo may be provided upstream or downstream of the two-dimensional imaging analysis stage, described in the background section above, so as to supplement the current instrumental imaging analysis of embryos. In particular, the present invention, when combined with the conventional imaging analysis, furthers the efficiency and effectiveness of the overall approach for classifying embryos according to their desirability, and thus is useful in mass selection of desirable embryos suitable for incorporation into manufactured seeds.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1A:
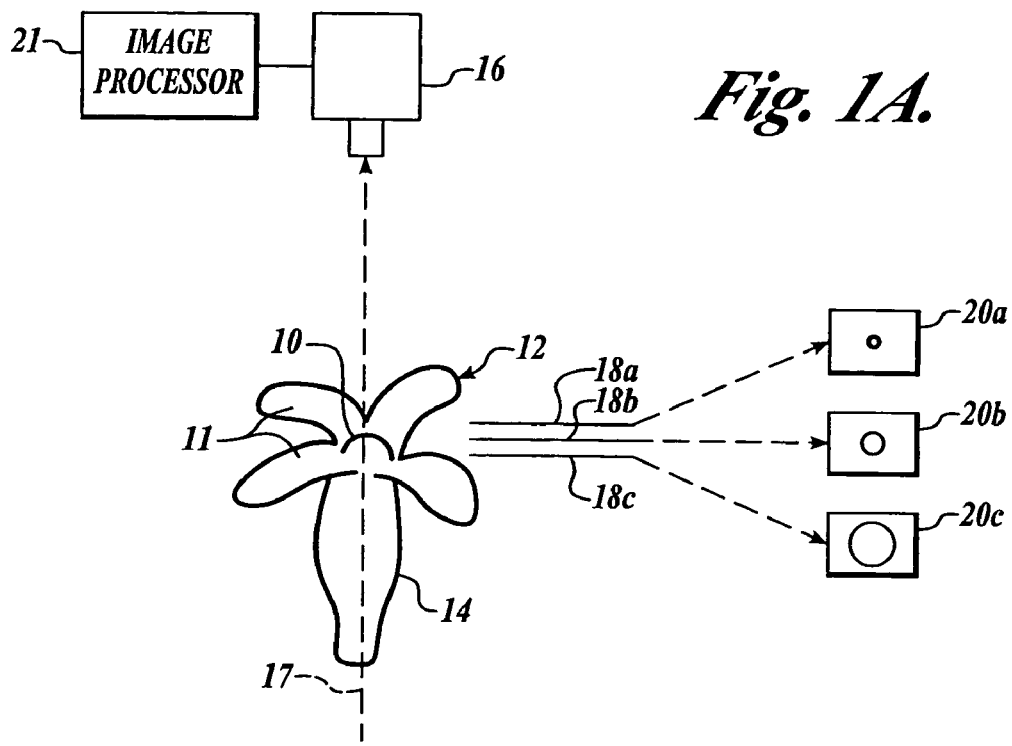
FIGS. 1A and 1B illustrate an embodiment of a method and system for obtaining three-dimensional information of an apical dome of a plant embryo, taking plural images of the apical dome at varying focal planes along an axis of the embryo.

Referring to FIG. 1A, the inventors have determined that the morphological features of an apical dome 10 located at the cotyledon end 12 of an embryo 14 are reliable indicators of the embryo's germinant vigor, i.e., potential for rapid epicotyl development after germination. An apical dome, or the apical meristem of a shoot, is the location where the cells that produce the leaf primordia of the shoot are formed. The rib meristem at the base of the dome produces the other primary shoot tissues. As used in the present description, a "shoot" is that part of a unit of a totipotent plant tissue that develops into the aerial portions of the plant, and includes the cotyledon(s), epicotyl, and/or hypocotyl. Cell division occurs at a very rapid rate in an actively growing shoot and these cells in turn elongate or expand, resulting in growth in length of the shoot. Leaf primordia 11 arise on the sides of the apical dome. As it has been found that the apical dome is critical to rapid epicotyl development after germination, its morphological features (size, shape, color, surface texture, etc.) are determined to be reliable indicators of the embryo's quality. In particular, the dome's morphological features are determined to be predictive of its post-germination early growth rate in the first month or so. In general, it has been determined that the bigger and more symmetrical the dome is, the more likely the embryo will grow rapidly after germination, though other morphological features of an apical dome may also be used as indicators of the embryo's desirability.

The present invention is directed to three-dimensionally imaging the apical dome of a plant embryo, for the purpose of classifying embryos according to their desirability (e.g., likelihood to rapidly develop epicotyl upon germination) based on the ascertained morphological features of the apical dome. According to a method of the invention, first, an apical dome at the cotyledon end of a plant embryo is three-dimensionally imaged. Next, various morphological features of the apical dome are ascertained based on the three-dimensional imaging, using suitable image recognition/analysis software known to one skilled in the art. The morphological features of a dome include the size (volume), shape, color, surface texture, etc. Lastly, the ascertained morphological features are used to classify embryos according to their desirability. This last step may be carried out according to a classification method as disclosed in PCT application Ser. No. PCT/US99/12128 (WO 99/63057), discussed above. This PCT application describes a method of developing a classification model based on an analysis of sample plant embryos of known morphological features and known quality.

Various methods are possible to three-dimensionally image an apical dome. In one embodiment, still referring to FIG. 1A, a method involves using a camera 16 arranged generally along an axis 17 of the embryo 14 and facing the apical dome 10. The camera 16 is focused at a first focal plane 18a to take a first image 20a of the apical dome 10, then is focused at a second focal plane 18b to take a second image 20b of the apical dome 10, then is focused at a third focal plane 18c to take a third image 20c of the apical dome 10, and so forth. Suitable arrangement to minimize any out-of-focus information (on either side of the focal plane) may be provided. The images 20a, 20b, and 20c taken at varying focal planes along the axis 17 of the embryo 14 are thereafter forwarded to and processed (e.g., combined) in an image processor 21, to provide three-dimensional information of the apical dome 10. For example, the two-dimensional images 20a, 20b, and 20c may be combined to compose a single three-dimensional image of the dome 10 indicating its height and diameter.

Any suitable camera 16 may be used, preferably a digital camera containing a charge-coupled device (CCD) linked to a digital storage device, so as to permit subsequent digital processing of the acquired image. Further, it should be understood that the images of an apical dome 10 may be taken by any image detector (not limited to a camera), perhaps being coupled to suitable image-processing or image-rendering software. For example, referring to FIG. 1B, one specific application of the above described multiple-focal-plane method is a Laser Scanning Confocal Microscopy (LSCM), as well known in the art, which uses a photodetector or a photomultiplier 22 to detect light reflected from an object at varying focal planes 18. In LSCM, a laser beam scans the sample and three-dimensional reconstruction of the sample is accomplished using image-rendering software. Specifically, illumination light (laser) from a light source 26 passes through an illumination pinhole 27 towards a dichroic mirror (beam splitter) 28, which redirects the light toward an objective lens 30. The lens 30 focuses the light on a focus point on a focal plane 18, and the image at the focus point is reflected to be transmitted via the lens 30, through the dichroic mirror 28, to a detector pinhole 32 to be received by the photodetector 22. At this time, any out-of-focus information, represented in broken lines 31, is substantially obstructed by the detector pinhole 32. The reflective, in-focus light received by the photo detector 22 is then converted into digital signals to produce a pixel-based digital image. Laser scanning is carried out at varying focal planes 18 (as indicated by an arrow 34), by moving the microscope stage with a computer-controlled fine-stepping motor in as little as 0.1 micron increments. A three-dimensional reconstruction of the sample can be generated by stacking two-dimensional sections collected in series.

Figure 2:
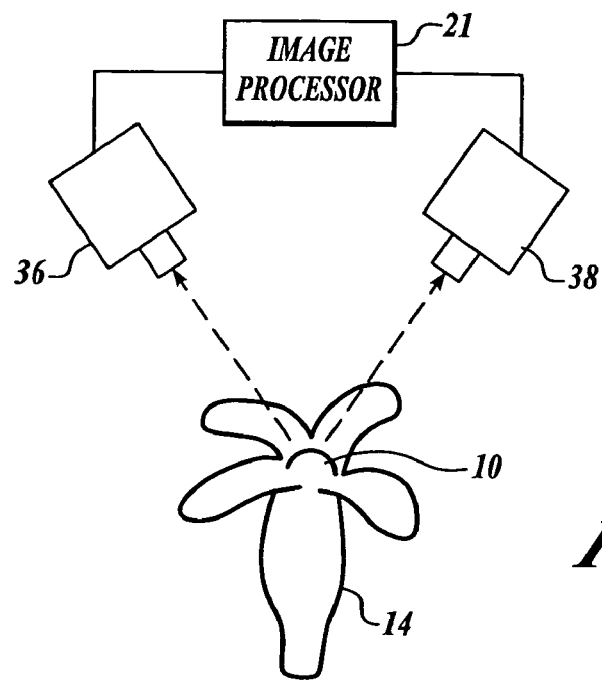
FIG. 2 illustrates another embodiment of a method and system for obtaining three-dimensional information of an apical dome of a plant embryo, using plural cameras arranged in a confocal manner to take plural images of the apical dome, respectively.

Referring to FIG. 2, in another embodiment, a method of three-dimensionally imaging an apical dome involves using a plurality of cameras 36 and 38 that are arranged at an angle in a confocal manner to take images of the apical dome 10, respectively. As used herein, "confocal manner" refers to an arrangement in which two imaging systems (e.g., two cameras) share a focal point. Specifically, the plurality of cameras 36 and 38 are arranged so that their respective object planes (i.e., planes containing the object to be imaged) are at an angle with respect to each other. The images obtained by these plurality of cameras 36 and 38 can be thereafter processed in combination by an image processor 21 to provide three-dimensional information of the apical dome 10. It should be understood that two or more cameras may be used with their objecting planes arranged at an angle with respect to each other.

Figure 1B:
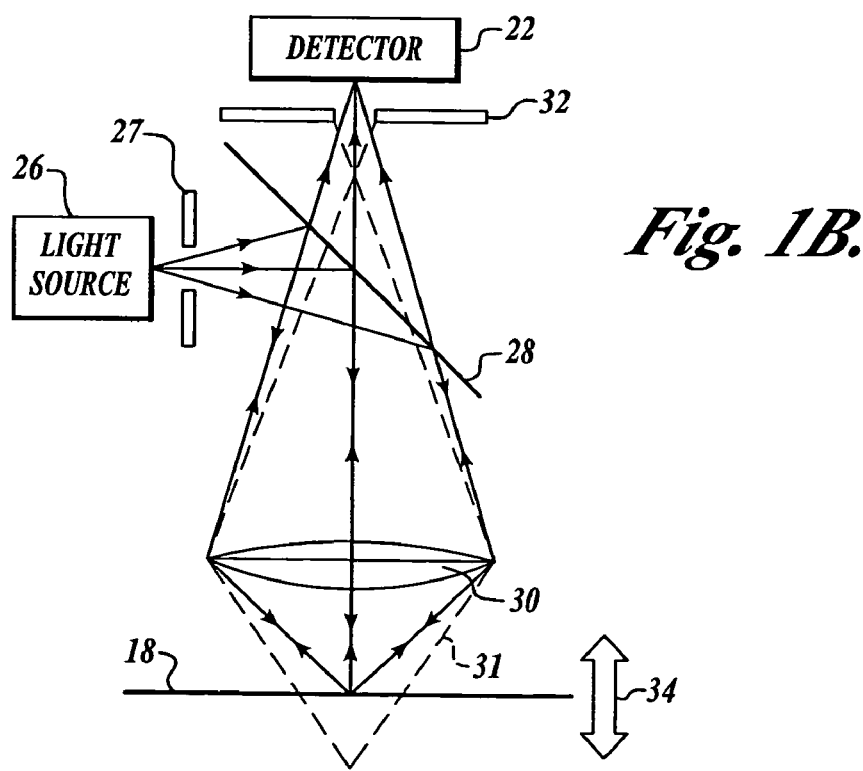
Figure 3:
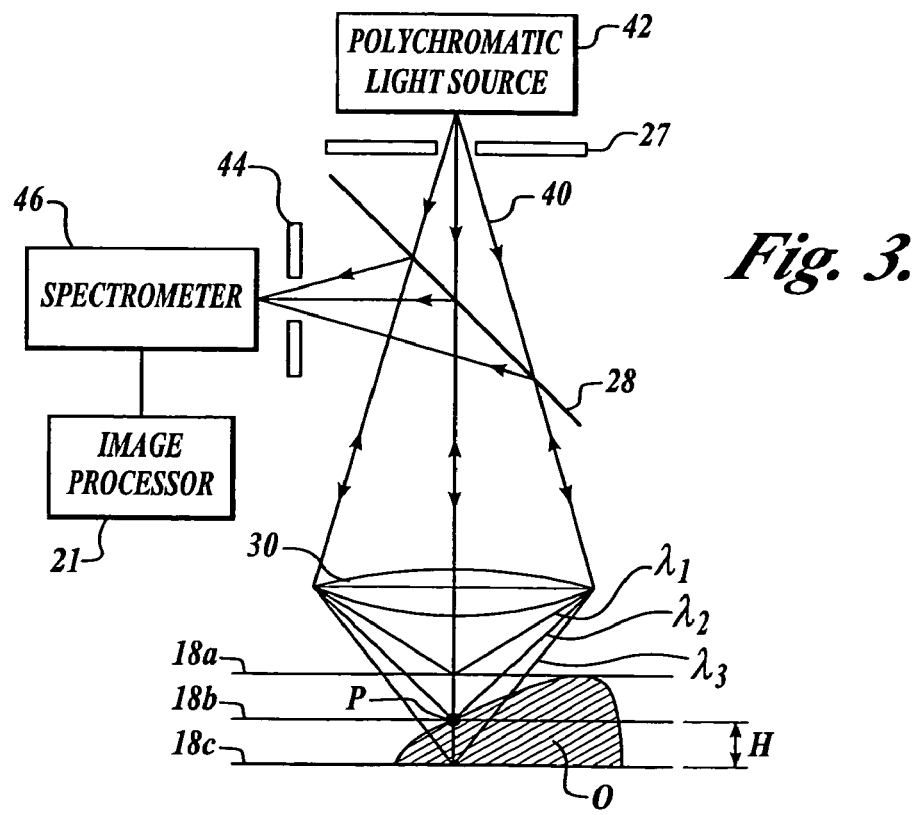
FIG. 3 illustrates yet another embodiment of a method and system for obtaining three-dimensional information of an apical dome of a plant embryo, simultaneously taking plural "images" of the apical dome at plural wavelengths focused at plural focal planes, respectively.

In yet another embodiment, referring to FIG. 3, a method of three-dimensionally imaging an apical dome of a plant embryo involves Quasi Confocal Extended Field Surface Sensing (QCEFSS), as well known in the art. This method essentially takes advantage of the chromatic aberration generally encountered in a classical confocal setup, such as LSCM described in FIG. 1B above, when using a polychromatic point source. Specifically, white light 40 from the polychromatic point source 42 passes through the illumination pinhole 27 and a beam splitter 28 toward the objective lens (with chromatic aberration) 30 and is focused. At this time, light beams at varying wavelengths $\lambda 1$, $\lambda 2$, and $\lambda 3$ are focused at varying focal planes 18a, 18b, 18c, respectively. However, at any given point along an axial field of view, there is only one wavelength perfectly focused. For example, in the illustrated embodiment, only the light beam at wavelength $\lambda 2$ is focused at a surface point P of the object O that intersects with the focal plane 18b. The focused light at wavelength $\lambda 2$ is thus reflected back via the lens 30 and the beam splitter 28 toward a pinhole (spatial filter mask) 44 and then to a spectrometer 46, while all out-of-focus information (e.g., light at wavelengths $\lambda 1$ and $\lambda 3$) is blocked by the pinhole 44. Accordingly, by two-dimensionally scanning the object O in this manner, QCEFSS can obtain a series of monochromatic images, with each monochromatic image corresponding to a certain height H of the object. A suitable image processor 21 can be used to combine these monochromatic images to obtain accurate height information of the object, with resolution of the order of 1 nm. Unlike a classical confocal setup as shown in FIG. 1B, the QCEFSS method does not require varying the focal plane because light beams of multiple wavelengths are simultaneously focused at multiple focal planes (though only one wavelength is actually focused at a particular surface point of an observed object). Suitable QCEFSS equipment may be available from Sciences et Techniques Industrielles de la Lumiere of France.

It should be understood that other suitable optical metrology or microtopographic methods, as apparent to one skilled in the art, may be used to obtain three-dimensional information of an apical dome of a plant embryo, including the use of a differential interferometer, spectroscopic reflectometry, etc.

In one embodiment, a system of the present invention for obtaining three-dimensional information of an apical dome of a plant embryo may be incorporated into an automated manufactured seed delivery/manufacturing line, as disclosed in PCT application Ser. No. PCT/US00/40720 (WO 01/13702 A2), discussed above. For example, any of the embodiments for obtaining three-dimensional information of an apical dome, as described above, may be placed along a conveyor belt for delivering embryos, so that an apical dome of an embryo can be three-dimensionally imaged for analysis, as part of the overall embryo delivery/manufacturing line. As described above, the delivery/manufacturing line typically includes an imaging camera, which acquires and digitally stores two-dimensional images of embryos (e.g., the top view, the side view, and the end view of each embryo) for the purpose of classifying embryos according to their desirability. A system of the present invention for three-dimensionally imaging an apical dome of each embryo may be provided upstream or downstream of the two-dimensional imaging stage, so as to supplement the current instrumental imaging analysis to further the efficiency and effectiveness of the overall approach for classifying embryos. In particular, the present invention is useful in mass selection of desirable embryos suitable for incorporation into manufactured seeds, and hence in mass production of manufactured seeds.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method of three-dimensionally imaging an apical dome of a plant embryo, comprising:
   obtaining three-dimensional information of the apical dome of the plant embryo with an image detector or a spectrometer;
   ascertaining at least one morphological feature of the apical dome based on the obtained three-dimensional information with image recognition and/or analysis software running on a computer; and
   classifying the plant embryo according to its putative germinant vigor based on the at least one ascertained morphological feature of the apical dome with a classification algorithm running on a computer, wherein the at least one morphological feature is selected from the group consisting of apical dome size, apical dome volume, apical dome shape, apical dome symmetry, apical dome color, and apical dome surface texture.

2. The method of claim 1, wherein the morphological features include one or more of the size, shape, color, and surface texture of the apical dome.

3. The method of claim 1, wherein the morphological features comprise the size of the apical dome, and an embryo with a larger-sized apical dome is classified to have relatively greater putative germinant vigor as compared to an embryo with a smaller-sized apical dome.

4. The method of claim 1, wherein the step of obtaining three-dimensional information of the apical dome comprises:
   providing an image detector relative to the apical dome of a plant embryo;
   using the image detector, taking a first image of the apical dome at a first focal plane along an axis of the embryo;
   using the image detector, taking a second image of the apical dome at a second focal plane along the axis of the embryo; and
   combining the first and second images to obtain the three-dimensional information of the apical dome.

5. The method of claim 4, wherein the image detector comprises a camera.

6. The method of claim 4, wherein the image detector comprises a photodetector and the method comprises the use of a Laser Scanning Confocal Microscopy system.

7. The method of claim 1, wherein the step of obtaining three-dimensional information of the apical dome comprises:
   providing a first image detector for taking a first image of the apical dome of the plant embryo;
   providing a second image detector for taking a second image of the apical dome in a confocal manner, wherein an object plane of the first image and an object plane of the second image are arranged at an angle; and
   processing the first and second images to obtain the three-dimensional information of the apical dome.

8. The method of claim 1, wherein the step of obtaining three-dimensional information of the apical dome comprises:
   providing a polychromatic light source, a dichroic mirror, a lens, a filter, and a spectrometer relative to each other so that polychromatic light from the light source propagates via the dichroic mirror and the lens toward the apical dome and so that light reflected from the apical dome propagates via the lens and the dichroic mirror toward the filter and the spectrometer;
   irradiating the apical dome with the polychromatic light; and
   obtaining height information of the apical dome based on the reflected light received by the spectrometer.

9. The method of claim 1, wherein the plant embryo is a somatic embryo.

10. The method of claim 1, wherein the plant embryo is a conifer embryo.

11. The method of claim 1, further comprising classifying the plant embryo by comparing the morphological features to a pre-developed classification model, wherein the classification model is based on a sample of embryos of know morphological features and known quality.

12. A system for obtaining three-dimensional information of an apical dome of a plant embryo, comprising:
   an image detector positioned relative to the apical dome of the plant embryo, the image detector being configured to vary its focal plane along an axis of the embryo so as to take a first image of the apical dome at a first focal plane along the axis of the embryo and to take a second image of the apical dome at a second focal plane along the axis of the embryo;
   an image processor for combining the first and second images to obtain the three-dimensional information of the apical dome; and
   a computer with instructions to ascertain at least one morphological feature of the apical dome based on the obtained three-dimensional information and classify the plant embryo according to its putative germinant vigor based on the at least one morphological feature of the apical dome, wherein the at least one morphological feature is selected from the group consisting of apical dome size, apical dome volume, apical dome shape, apical dome symmetry, apical dome color, and apical dome surface texture.

13. The system of claim 12, wherein the image detector comprises a camera.

14. The system of claim 12, further comprising a Laser Scanning Confocal Microscopy system.

15. The system of claim 12, wherein the computer further comprises instructions for classifying the plant embryo by comparing the morphological features to a pre-developed classification model, wherein the classification model is based on a sample of embryos of know morphological features and known quality.

16. A system for obtaining three-dimensional information of an apical dome of a plant embryo, comprising:
   a first image detector for taking a first image of the apical dome of the plant embryo;
   a second image detector for taking a second image of the apical dome in a confocal manner, wherein an object plane of the first image and an object plane of the second image are at an angle;
   an image processor for processing the first and second images taken by the first and second image detectors, respectively, to obtain the three-dimensional information of the apical dome; and
   a computer with instructions to ascertain at least one morphological feature of the apical dome based on the obtained three-dimensional information and classify the plant embryo according to its putative germinant vigor based on the at least one morphological feature of the apical dome, wherein the at least one morphological feature is selected from the group consisting of apical dome size, apical dome volume, apical dome shape, apical dome symmetry, apical dome color, and apical dome surface texture.

17. The system of claim 16, wherein the first and second image detectors comprise cameras.

18. The system of claim 16, wherein the computer further comprises instructions for classifying the plant embryo by comparing the morphological features to a pre-developed classification model, wherein the classification model is based on a sample of embryos of know morphological features and known quality.

19. A system for obtaining three-dimensional information of an apical dome of a plant embryo, comprising:
   a polychromatic light source, a dichroic mirror, a lens, a filter, and a spectrometer arranged relative to each other so that polychromatic light from the light source propagates via the dichroic mirror and the lens toward the apical dome and so that light reflected from the apical dome propagates via the lens and the dichroic mirror toward the filter and the spectrometer;
   a processor for obtaining height information of the apical dome based on the reflected light received by the spectrometer; and
   a computer with instructions to ascertain at least one morphological feature of the apical dome based on the obtained height information and classify the plant embryo according to its putative germinant vigor based on the at least one morphological feature of the apical dome, wherein the at least one morphological feature is selected from the group consisting of apical dome size, apical dome volume, apical dome shape, apical dome symmetry, apical dome color, and apical dome surface texture.

20. The system of claim 19, wherein the computer further comprises instructions for classifying the plant embryo by comparing the morphological features to a pre-developed classification model, wherein the classification model is based on a sample of embryos of know morphological features and known quality.

* * * * *